Figure 1:
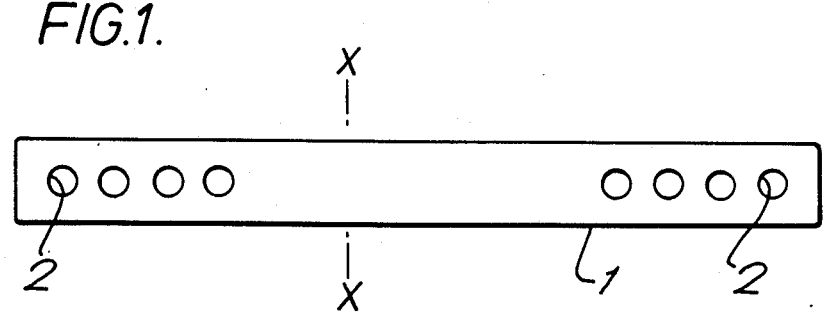

United States Patent [19]

Spector et al.

[11] Patent Number: 4,773,406

[45] Date of Patent: Sep. 27, 1988

[54] BONE FRACTURE FIXATION PLATES

[75] Inventors: Myron Spector, Atlanta; John D. Muzzy, Marietta, both of Ga.

[73] Assignee: Ed. Geistlich Sohne AG fur Chemische Industrie, Lucerne, Switzerland

[21] Appl. No.: 70,148

[22] Filed: Jul. 2, 1987

Related U.S. Application Data

[63] Continuation of Ser. No. 881,575, Jul. 2, 1986, abandoned, which is a continuation of Ser. No. 690,054, Jan. 9, 1985, abandoned.

[30] Foreign Application Priority Data

Jan. 13, 1984 [GB] United Kingdom ............... 8400932

[51] Int. Cl.⁴ ............................... A61F 5/64
[52] U.S. Cl. ................... 128/92 YL; 128/92 YP; 128/92 YE
[58] Field of Search ............... 128/92 AL; 3/1.9

[56]  References Cited

U.S. PATENT DOCUMENTS 3,744,488  7/1973  Cox ............................... 128/92 BC
4,279,249  7/1981  Vert et al. ....................... 128/92 YQ
4,338,926  7/1982  Kummer et al. .................. 128/92 R
4,356,572 11/1982  Guillemin ........................ 128/92 BC

OTHER PUBLICATIONS

DePay "Fracture Appliances", 1954, p. 124A.
Tayton, et al., *The Journal of Bone and Joint Surgery*, vol. 64-B, No. 1, pp. 105-111, 1982.
Akeson, et al., *Acta Orthop*, vol. 47, No. 3, pp. 241-249, 1976.
Woo, et al., *The Journal of Bone and Joint Surgery*, vol. 58A, pp. 190-195, 1976.
Bradley, et al., *The Journal of Bone and Joint Surgery*, vol. 61-A, No. 6, pp. 866-872, 1979.
Bradley, et al., *Biomaterials*, vol. 1, pp. 38-40, 1980.
Claes, et al., 9th Annual Meeting of the Society for *Biomaterials*, p. 46, 1983.
Gillet, et al., 9th Annual Meeting of the Society for *Biomaterials*, p. 48, 1983.
Tunc, et al., 9th Annual Meeting of the Society for *Biomaterials*, p. 47, 1983.
Langrana, et al., *Proc. 29th Annual ORS*, Anaheim, CA, 1983.
Woo, et al., *Journal of Biomedical Materials Research*, vol. 17, pp. 427-439. 1983.

*Primary Examiner*—John Weiss
*Attorney, Agent, or Firm*—Bernard, Rothwell & Brown

[57]  ABSTRACT

A bone fracture fixation device for fixation to a fractured bone is substantially free from resorbable materials and materials which soften on exposure to body fluids, and undergoes a gradual decrease in rigidity over the healing period of the fracture.

13 Claims, 1 Drawing Sheet

BONE FRACTURE FIXATION PLATES

This application is a continuation of application Ser. No. 881,575 filed July 2, 1986, now abandoned which is a continuation of application Ser. No. 690,054 filed Jan. 9, 1985, now abandoned.

BACKGROUND OF THE INVENTION

1. Field of the Invention

This invention relates to improvements in or relating to bone fracture fixation plates and related devices.

2. Description of the Background Art

Fixation of bone fractures in humans is commonly achieved by the use of a plaster cast to prevent undue relative movement of the fracture ends of the bone. With the cast in place, the fractured bone reunites with a large amount of callus being formed about the fracture site. After the plaster cast is removed, the reunited bone is initially allowed only a limited load bearing function whereafter there is a gradual return to the normal load bearing function.

However, with the use of plaster casts, there is difficulty in obtaining adequate reduction of the fracture and there is a tendency for the joints on either side of the fracture to stiffen and for the muscle surrounded by the cast to atrophy. In addition, this method of treatment is contraindicated for use with open fractures. Within recent decades there has therefore developed significant use of an alternative fracture fixation method, internal fixation, in which a rigid plate is secured to the fractured bone to span the fracture thereby aligning the fractured ends of the bone for union and removing the load bearing function from the fractured section of the bone.

The major efforts in the development of internal fixation have been towards a rigid fixation whereby a bone fracture fixation plate or internal fixation plate of a rigid material such as stainless steel is securely attached to the bone to hold the fractured ends together without relative movement. This approach has the great advantage that the bone can be brought under normal load very quickly, thus aiding the healing process and greatly reducing the period of incapacitation of the patient.

This rigid fixation with a metal plate with mechanical stiffness in excess of that of the bone results in a primary end-to-end union of the fractured ends with little or no callus formation. However, the healing process is normally accelerated by moderate flexure of the bone about the fracture site and consequently with such rigid fixing methods primary union in humans is slow, taking about 12 to 24 months. During such a prolonged period of healing and after the fracture has been united the bone shielded from strains (stresses) by the plates may undergo osteopenia, i.e. bone porosity may increase and cortical thickness may decrease, which may result in refracture following removal of the plate. The shielding of bone from strain (stress) as a result of rigid fixation is termed stress shielding. Alternatively, if fractured bone ends fixed by conventional metal plates are separated by some gap, their motion under repeated loading may lead to sudden plate fatigue failure during the healing period, disrupting the healing process.

Furthermore, conventional metal plates are somewhat disadvantageous as they may release undesirable metal ions and can adversely affect cells, tissues and organs, particularly over the long healing periods mentioned above. They therefore normally require removal in a second surgical operation as soon as is feasible.

Alternative methods of fixation employ metal rods (pins) inserted into the medullary canal of the fractured long bone to achieve alignment of the fractured bone ends. Disadvantages of this include metal ion release and a bending rigidity that may shield surrounding bone from stress once the fracture is united.

In an attempt to avoid these problems, there have been developed plates, generally glass or carbon fibre reinforced polymer composites, of lower rigidity than conventional stainless steel plates. Such plates however have not so far proved entirely satisfactory since it is difficult to attain a balance between the relatively high rigidity of fixture of the fractured ends required in the initial stages of healing and the lower degree of rigidity of fixture required in the later stages of healing to promote the healing process and avoid stress shielding and osteopenia. On the one hand there is a danger that these polymer plates, which have rigidities closer to that of the bone than that of conventional metal plates, will not have sufficient strength to support applied loads before the fracture heals sufficiently to provide some rigidity in the bone itself. On the other hand if the plates are more rigid than the reunited bone there is still the danger of stress shielding; because different bones in different individuals vary in stiffness it will never be possible to fabricate a plate that exactly matches the stiffness of a particular bone.

Recently, there have been investigations into the use of absorbable materials as internal fixation plates. These plates rely on the dissolution or resorption of the plates within the body so that by the time the fracture is healed little or none of the original plate remains. Thus for example Tunc et al (Proc. 9th Int. Meeting of the Soc. for Biomaterials (1983) 47) have disclosed the use of plates comprising totally absorbable high molecular weight polylactide polymer. Alexander et al. (Trans. 11th Int'l Biomat. Symp. 11 (1979)) have disclosed plates of absorbable polylactic acid polymer reinforced with carbon fibres. Parsons et al. (5th Annual Meeting of the Society for Biomaterials (1979)) have disclosed plates comprising absorbable polylactic acid polymer reinforced with continuous carbon fibres. Vert et al. (U.S. Pat. No. 4,279,249) have disclosed plates of absorbable polylactic acid polymer reinforced with absorbable polyglycolic acid polymer.

However, the biological response which results in the resorption of such plates in the body creates further problems. Thus this biological response may not be sufficiently specific to resorb only the plates and can also cause destruction of the underlying bone and of soft tissue in the vicinity. Furthermore, substances released by the resorption of the plates may accumulate at such sites as lymph nodes and cause adverse tissue changes. Moreover, non-resorbable fibre reinforcement material released from the resorbable matrix of a fibre reinforced resorbable plate may be dispersed throughout the tissue of the patient.

A further line of approach has been to use composite systems comprising rigid and resorbable components in which, on resorption of the resorbable component, the rigid component is freed of its load bearing function. This can occur suddenly as with the fracture clamp of U.S. Pat. No. 2,987,062 which comprises two metallic bands directly connected at one pair of ends and joined by absorbable catgut at the other pair of ends. Loss of rigidity can also occur gradually as with the plates of U.S. Pat. No. 4,338,926 in which a rigid plate secured by screws to the fractured bone is provided with a resorbable element lying between the rigid plate and the bone or the securing screws, upon the resorption of which element the attachment of the rigid plate is loosened and its load bearing function is lost. In the case where the composite system looses its load bearing function suddenly, there are on the one hand the obvious dangers of system failure before fracture reunion is completed thus subjecting the incompletely healed bone to the full stress of normal load bearing and on the other hand the dangers of osteopenia if the composite system does not yield its load bearing function until a relatively long time after fracture reunion is completed. In the second case, as with the resorbable plates discussed above, significant amounts of resorbable material are released into the body by the composite system will all the possible dangers that that entails.

SUMMARY OF THE INVENTION

We have found that it is possible to design a bone fracture fixation device which overcomes the above problems by being capable of gradual decrease in rigidity while attached to a fractured bone and yet does not release substantial amounts of resorbable material into the body.

In one aspect, the present invention thus provides a bone fracture fixation plate or similar device which is substantially free from resorbable components and is capable in use of a gradual decrease in rigidity over the fracture healing period from a rigidity close to or in excess of that of the intact bone to a rigidity significantly below that of the intact bone.

In a further aspect, the present invention provides a method of treating human or animal bone fractures which method comprises securing to a fractured bone to span the fracture a bone fracture fixation plate or similar device which is substantially free from resorbable components and is capable in use of a gradual decrease in rigidity over the fracture healing period from a rigidity close to or in excess of that of the intact bone to a rigidity below that of the intact bone with the rigidity of the plate remaining greater than that of the healing bone until the bone has reached a load bearing rigidity.

The plates of the invention are conveniently either plates whose rigidity decreases through mechanical fatigue as a result of repeated loading during the fracture healing period or plates having components which are softened but not resorbed by the action of body fluids thereby reducing the rigidity of the plate as a whole.

In the first category, the plates of the invention may conveniently be formed from high strength fibre reinforced polymers in whose formation coupling agents have not been employed to obtain chemical bonding between the polymer matrix and the reinforcing fibres. Under the repeated loading resulting from near-normal use of the bone, microscopic separations between the fibres and the polymer matrix occur causing the rigidity of the plate to decrease. In this respect, high strength thermo-plastic polysulphones reinforced by short fibres and continuous strands of carbon and glass are particularly preferred materials. Alternatively, coupling agents susceptible to mechanical breakdown with exposure to body fluids and repreated loading may be used to obtain initial bonding between the poylmer matrix and the reinforcing fibres. In this respect silyl reactive polysulphone may be used as the coupling agent for a polysulphone polymer matrix.

In another embodiment, plates, either of conventional metal or alloy or of rigid synthetic resin, can be notched transversely or provided with a porous structure. Repeated loading causes the notches to extend or the voids in the porous structure to enlarge and the rigidity of the plate to decrease gradually.

In a preferred embodiment, the plates of the invention are of laminate construction with at least two laminae being bonded together only to a predetermined extent, for example by the use of a cyanoacrylate adhesive. The plates may, for example, be made of carbon-fibre reinforced polysulphone. Repeated stress loading results in progressive failure of the interlaminar bond and a decrease in the rigidity of the plate as a whole. In one embodiment, the polysulphone laminae may merely be joined by heat and/or compression bonding, which will commonly be incomplete and subject to gradual failure on flexure of the plate. Thus, in one useful embodiment, laminae of unreinforced polysulphone may be placed between laminae of reinforced polysulphone and bonded by heating under compression. In another embodiment, a thermoplastic resin may be applied in particulate form to one of the laminae, so that on heat bonding the laminae are joined intermittently by the melted particles. This type of embodiment is particularly favourable since laminar thicknesses may readily be selected which when the laminae are bonded together results in a maximum rigidity in excess of that of the intact bone and which when the bond between the laminae fails results in a minimum rigidity somewhat beneath the rigidity of the intact bone. Furthermore, we have found that after long periods of flexing, the axial rigidity of plates of this type may be reduced while the bending rigidity is substantially unchanged. This may be advantageous as explained hereinafter. A range of plates of graded initial and final rigidities and rates of rigidity decrease can thus be made available to the surgeon to deal with virtually all bone-setting requirements.

It should be noted that while the rigidity of plates of this type is decreased significantly, adequately tensile strength is maintained.

A major advantage of this type of construction is that the loading and flexure of the bone at the fracture site leads both to accelerated healing of the fracture and to the desired gradual decrease in rigidity of the bone plate. Thus, the healing process and the decrease in the rigidity of the supporting plate tend to proceed at a greater or lesser rate according to the amount of loading to which the bone is exposed.

In an alternative construction, the plates according to the invention weaken under the action of body fluids but without loss of material by resorption. Thus for example the plates may be of a composite form comprising a plate, for example of fibre-reinforced polymer, in which material removed from the centre section of the plate, for example by the formation of apertures therein, is replaced by a substance which softens gradually on exposure to body fluids, for example an aqueous gel comprising polyacrylamide polymerised in the presence of a non-resorbable gel-forming material such as agarose; the rigidity of the plates with the filler substance in the unsoftened state is above that of intact bone while the filler substance in the softened state is below that of intact bone.

Alternatively, the plate as a whole may be formed from non-resorbable, suitably reinforced, substances such as an aqueous gel of the above type which soften on exposure to body fluids. Such softenable material may also be used to bond laminar plates of the type mentioned above. Gradual softening of the bonding layer by penetration of body fluid at the edges of the plates, or via apertures in the outer layers, thus leads to a gradual decrease in rigidity.

Where such an aqueous gel is used, it may be advantageous for this to carry one or more medicaments which, on delayed release during the healing period, can assist healing and/or avoid or minimise infection. One particularly useful medicament in this context is taurolidine, which is active against bacterial infections and also against bacterial toxins which can have a deleterious effect on bone tissue.

In another embodiment, laminae of the plates may be bonded together with adhesives such as urethanes or acrylamides which break down mechanically under repeatedly loading. Fibrin adhesive, which degrades with exposure to body fluids and under repeated loading, may also be used as an adhesive to bond together the laminae of laminated plates according to the invention.

It will be appreciated that the bone fracture fixation plates according to the invention may comprise more than one of the features or embodiments referred to above.

In general, the plates according to the invention will be of conventional shape and size. For the majority of fractures, the plates will be relatively long narrow strips, provided with holes to accommodate screws at appropriate intervals. There will normally be an area equidisant form the ends of the plate which will be intended to be sited close to the fracture and which will be free from screw holes, while the latter holes will normally be in areas nearer to the ends.

In that the stresses on the plates are particularly high in the areas close to the screw holes, it may be desirable to reinforce these areas, for example by including additional fibre reinforcement.

The plates according to the invention may, in use, show a gradual reduction in axial, torsional and/or bending rigidity. It has been demonstrated by Woo et al. (J. of Biomedical Materials Research 17 (1983) 427-439) that osteopenia resulting from internal fixation of fractures is reduced by the use of plates which are of reduced axial stiffness, although of torsional and bending stiffnesses comparable to those of conventional metal plates. Accordingly, the plates of the present invention may advantageously be formed to be capable of gradual degradation in axial rigidity over the fracture healing period with a relatively lower or no degradation in the same period of the torsional and/or bending rigidity.

The fixation members (plates and rods (pins) of the invention, or the rigid components of composite plates according to the invention,) are advantageously non-metallic allowing the members to be left attached to the bone after healing is complete rather than making necessary a second surgical operation for plate removal. Suitable materials include synthetic resins such as polysulphones, polyphenyl sulphones, epoxies, acrylic resins, polyolefins, polyoxymethylene, polyphenylene sulphide, polyetherketones, polyamides and polyesters, preferably reinforced with carbon, glass and/or other high-strength synthic fibres.

The rigidity of each individual plate or rod will depend on its intended mode and position of use. For use with fractures of the human femur, axial rigidities in the range 2 to 6 $Nm^2$ are generally useful.

In general, the plates according to the invention will be used in the conventional way. Where additional rigidity is required, two such plates may be applied to the fractured bone, normally spaced at about 90° in the circumferential direction. Plates composed of thermoplastic polymeric materials may be conformed to shape of the bone concerned by thermoforming in the operating theatre without significant change in the expected decrease in rigidity over the fracture period.

The intramedullary rods (pins) according to the invention in general will be of conventional shape and size. For the majority of fractures, the rods will comprise a laminate of composite plastics.

Figure 2:
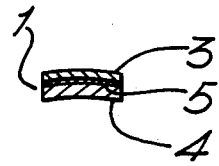

An embodiment of a bone fracture fixation plate in accordance with the present invention will now be described by way of example with reference to the accompanying drawing in which:

FIG. 1 represents a plan view of a bone fracture fixation plate according to the invention; and FIG. 2 represents a cross-section of the plate of FIG. 1 across the line X—X:

As shown in FIGS. 1 and 2, a bone fracture fixation plate for fixation to a fracture of a human femur in an adult male is approximately 140 mm by 14 mm by 4.5 mm and is provided with 8 apertures 2 for securing screws.

The plate comprises two layers of carbon fibre reinforced polysulphone 3 and 4 with dimensions 140 mm by 14 mm by 1.5 mm and 140 mm by 14 mm by 3 mm respectively laminated together with a layer 5 of cyanoacrylate adhesive available from B. Braun Melsyngen under the trade name HISTOACRYL.

About 16 weeks after fixation of the plate to the fractured bone, the stiffness of the plate will have dropped to about one half of its original level and the major load bearing function will be being taken over by the healing bone.

In a further embodiment of the invention, a plate similar to that shown in FIGS. 1 and 2 is made by assembly of 3 laminae of carbon fibre reinforced polysulphone. The dimensions of the laminae are 140 m by 14 mm by 1 mm. The carbon fibre reinforced laminae comprise polysulphone containing 40% of continuous Cellion 3000 carbon fibre threads (Celanese Corporation, Chatham, N.J., USA).

The polysulphone was Union Carbide Corporation P-1700-Medical Grade. Dantry Conneticutt. No bonding agent was employed. Bonding was effected by compression at 50 psi ($3.45 \times 10^5$ Pa) and 300° C. for twenty minutes followed by 100 psi ($6.9 \times 10^5$ Pa) and 150°-200° C. for 25 minutes.

The plate is desirably given a slight curvature in the lateral direction in order to conform to the surface of the bone.

Plates of the above type were subjected to $2 \times 10^5$ cycles of bending. It was found that the flexural modulus (and hence the bending rigidity) was reduced by about 15% while the tensile modulus (and hence the axial rigidity) was reduced by about 20%. The tensile strength remained substantially unchanged $3.6 \times 10^4$ psi ($2.5 \times 10^8$ Pa).

In a still further embodiment of the invention 2 laminae of carbon fibre reinforced polysulphone of the type described above, of dimensions 140 mm by 14 mm by 1 mm were provided with an intermediate layer of 1 mm of particles of the same polysulphone of average particle size approximately 0.4 mm and bonded at 100 psi ($6.9 \times 10^5$ Pa) and 250° C. for 30 minutes.

Plates of the above composite type were subjected to $2 \times 10^5$ cycles of bending. It was found that the flexural modulus (and hence the bending rigidity) remained substantially unchanged but that the tensile modulus (and hence the axial rigidity) was reduced by about 35%. However, the tensile strength remained unchanged, at about $2.2 \times 10^4$ psi ($1.5 \times 10^8$ Pa). Thus, composites of this type are capable of meeting the requirements referred to above wherein only the axial rigidity is substantially reduced over the healing period of the fracture.

We claim:

1. A bone fracture fixation device, comprising a fixation member for fixation to a fractured bone, which fixation member undergoes a gradual decrease in rigidity over the fracture healing period, said fixation member being substantially free from resorbable materials and being substantially free from materials which soften on exposure to body fluids.

2. A device as claimed in claim 1 composed of high strength fibre reinforced polymers containing no coupling agent between the fibres and the polymer.

3. A device as claimed in claim 1 comprising at least two laminae bonded together by an intermittent interlaminar bond, said intermittent interlaminar bond comprising melted particles of a thermoplastic resin, so that repeated loading results in progressive failure of the interlaminar bond.

4. A device as claimed in claim 1 comprising at least two laminae in which the laminae are bonded by a cyanoacrylate adhesive.

5. A device as claimed in claim 3 or 4 which is capable of a gradual decrease in axial rigidity over the fracture healing period while its bending rigidity is not substantially reduced.

6. A device as claimed in claim 1 which is a fracture fixation plate.

7. A device as claimed in claim 2, wherein the polymer is polysulphone, the reinforcing fibres are carbon fibres and there is no coupling agent between the fibres and the polymer.

8. A method of fixation of a bone fracture which comprises securing to the bone at points spanning said fracture a bone fracture fixation device which is substantially free from resorbable materials and materials which soften on exposure to body fluids, said device comprising a fixation member for fixation to a fractured bone, which fixation member undergoes a gradual decrease in rigidity over the fracture period.

9. A method as claimed in claim 8, wherein said bone fracture fixation device is composed of high strength fibre reinforced polymers containing no coupling agent between the fibres and the polymer.

10. A method as claimed in claim 9, wherein the polymer is polysulphone, the reinforcing fibres are carbon fibres and there is no coupling agent between the fibres and the polymer.

11. A method as claimed in claim 8, wherein the bone fracture fixation device comprises at least two laminae bonded together by an intermittent interlaminar bond, said intermittent interlaminar bond comprising melted particles of a thermoplastic resin, so that repeated loading results in progressive failure of the interlaminar bond.

12. A method as claimed in claim 9, wherein the bone fracture fixation device comprises at least two laminae in which the laminae are bonded by a cyanoacrylate adhesive.

13. A method as claimed in claim 8, wherein the bone fracture fixation device is a fracture fixation plate.

* * * * *

UNITED STATES PATENT AND TRADEMARK OFFICE
CERTIFICATE OF CORRECTION

PATENT NO. : 4,773,406

DATED : SEPTEMBER 27, 1988

INVENTOR(S) : MYRON SPECTOR, ET AL.

It is certified that error appears in the above-identified patent and that said Letters Patent is hereby corrected as shown below:

```
Column 3, line 17, delete "will" and substitute
    therefor -- with --;

Column 5, line 56, delete ",)" and substitute
    therefor -- ), --.
```

Signed and Sealed this

Thirteenth Day of February, 1990

Attest:

JEFFREY M. SAMUELS

Attesting Officer     Acting Commissioner of Patents and Trademarks